(12) United States Patent
Zhang et al.

(10) Patent No.: US 11,091,734 B2
(45) Date of Patent: Aug. 17, 2021

(54) PLATED YEAST FORMULATIONS

(71) Applicant: Firmenich SA, Geneva (CH)

(72) Inventors: Fei Zhang, Shanghai (CN); Pierre-Etienne Bouquerand, Geneva (CH); Anita Gaudin, Geneva (CH)

(73) Assignee: Firmenich SA, Satigny (CH)

( * ) Notice: Subject to any disclaimer, the term of this patent is extended or adjusted under 35 U.S.C. 154(b) by 67 days.

(21) Appl. No.: 16/311,802

(22) PCT Filed: Jun. 30, 2017

(86) PCT No.: PCT/EP2017/066334
§ 371 (c)(1),
(2) Date: Dec. 20, 2018

(87) PCT Pub. No.: WO2018/002331
PCT Pub. Date: Jan. 4, 2018

(65) Prior Publication Data
US 2020/0002666 A1  Jan. 2, 2020

(30) Foreign Application Priority Data

Jun. 30, 2016 (WO) ............... PCT/CN2016/087880

(51) Int. Cl.
| | | |
|---|---|---|
| *C12N 1/18* | (2006.01) | |
| *A23L 29/00* | (2016.01) | |
| *A23P 10/40* | (2016.01) | |
| *A23G 4/12* | (2006.01) | |
| *A23G 4/20* | (2006.01) | |
| *A61K 8/99* | (2017.01) | |
| *A61Q 13/00* | (2006.01) | |
| *A23L 27/00* | (2016.01) | |
| *A23P 10/30* | (2016.01) | |
| *A61K 8/73* | (2006.01) | |
| *B01J 13/02* | (2006.01) | |

(52) U.S. Cl.
CPC ............. *C12N 1/18* (2013.01); *A23G 4/12* (2013.01); *A23G 4/20* (2013.01); *A23L 27/72* (2016.08); *A23L 29/065* (2016.08); *A23P 10/30* (2016.08); *A23P 10/40* (2016.08); *A61K 8/73* (2013.01); *A61K 8/99* (2013.01); *B01J 13/02* (2013.01); *A61K 2800/56* (2013.01); *A61Q 13/00* (2013.01)

(58) Field of Classification Search
CPC . C12N 1/18; A23L 29/06; A23L 27/72; A23L 29/065; A23P 10/30; A23P 10/40; A23G 4/12; A23G 4/20; A61K 8/73; A61K 8/99; A61K 2800/56; B01J 13/02; A61Q 13/00; A23V 2002/00; A23D 9/007; C11B 15/00

See application file for complete search history.

(56) References Cited

U.S. PATENT DOCUMENTS

| | | | |
|---|---|---|---|
| 5,521,089 A | 5/1996 | Ishiguro et al. | |
| 2016/0015061 A1* | 1/2016 | Bouquerand | A23L 29/10 |
| | | | 426/61 |

FOREIGN PATENT DOCUMENTS

| | | | |
|---|---|---|---|
| JP | 2005211024 A | 8/2005 | |
| JP | 2008263925 A | 11/2008 | |
| JP | 2009518029 A | 5/2009 | |
| JP | 2007505619 A | 7/2011 | |
| JP | 2013215211 A | 10/2013 | |
| WO | 1993011869 A1 | 6/1993 | |
| WO | 2007066295 A2 | 6/2007 | |
| WO | 2011000524 A1 | 1/2011 | |
| WO | 2014128071 A1 | 8/2014 | |
| WO | WO-2014128071 A1 * | 8/2014 | ............. A23L 27/72 |
| WO | 2014206956 A1 | 12/2014 | |

OTHER PUBLICATIONS

Salari, R. et al. 2013. New aspects of *Saccharomyces cerevisiae* as a novel carrier for berberine. DARU Journal of Pharmaceutical Sciences. 21(1): 73. (Year: 2013).*
Horiba Scientific. 2015. Particle Size Distribution in Flavoring and Flavorants. Retrieved from: https://web.archive.org/web/20150514172756/https://www.horiba.com/uk/scientific/products/particle-characterization/applications/flavoring-and-flavorants/ (Year: 2015).*
International Search Report and Written Opinion, application PCT/EP2017/066334, dated Jun. 30, 2017.
Bakry et al., Comprehensive Reviews in Food Science and Food Safety, vol. 15, 2015, p. 143-18.

* cited by examiner

*Primary Examiner* — Kade Ariani
(74) *Attorney, Agent, or Firm* — Armstrong Teasdale LLP (57) ABSTRACT

Provided herein is a composition comprising: a) about 25% up to about 75% of a plasmolysed micro-organism by weight of the total weight of the composition; b) about at least greater than 20% up to about 60% by weight flavor or fragrance, of the total weight of the composition c) about 1% up to about 25% desiccant; d) about 4% up to about <10% water; wherein the mean particle size distribution by weight of the composition is about greater than 100 micrometer up to about 1 millimeter.

12 Claims, 1 Drawing Sheet

PLATED YEAST FORMULATIONS

CROSS-REFERENCE

This application is a 371 filing of International Patent Application PCT/EP2017/066334 filed 30 Jun. 2017, which claims the benefit of International Patent Application PCT/CN2016/087880, filed 30 Jun. 2016, the contents of which is hereby incorporated by reference in its entirety.

FIELD

The technical field relates to formulations of encapsulated flavors in plasmolysed organisms.

BACKGROUND

Delivery systems for the controlled release of flavor or fragrance compounds and methods of making them have been reported. Microcapsules made of organisms used to encapsulate flavors or fragrances are known. These product and processes have, amongst other limitations, limitations in the amount of the flavor or fragrance that can be encapsulated. The process of fabricating this dry microcapsule mostly involved some energy-intensive dehydrating step such spray-drying and lyophilization making it less cost-effective and environment-friendly.

SUMMARY

Provided herein is a composition comprising:
a) from about 25% up to about 75% of a plasmolysed micro-organism by weight of the total weight of the composition;
b) about at least greater than 20% up to about 60% by weight flavor or fragrance, of the total weight of the composition,
c) about 1% up to about 25% desiccant; and
d) about 4% up to about <10% water; wherein the mean particle size distribution by weight of the composition is about greater than 100 micrometer up to about 1 millimeter.

Also provided herein is a method of making a plated yeast cake composition comprising:
a) blending:
  i) a homogenous cake, wherein the cake is made by mixing, at a temperature that ranges from 20° C. to about 90° C.
    1) a plasmolysed micro-organism in an amount of from about 0.01% to about 90% by weight of the total weight of the cake, particularly about from 20% to about 65%
    2) a flavor or fragrance oil provided in an amount of from at least 0.01% up to about 60% by weight of the total weight of the cake, particularly about from 20% up to about 65%, by weight of the total weight of the cake, more particularly the micro-organism provided in a ratio to flavor or fragrance from about 0.6 to 1 to about 2 to 1 by weight; and
    3) water provided in an amount of from about 5% up to about 90%, more particularly from about 5% up to about 30%, by weight of the total weight of the cake; wherein the micro-organism to water ratio in the cake is provided in an amount, by weight, of about 4.5 to 1 to 0.5 to 1, more particularly about 4.5 to 1 to 1 to 1;
  ii) at least about 50% up to about 99.9%, by weight desiccant, of the total weight of the composition to form a blended powder or uniform mixture;
  iii) optionally from about 0.2 to about 2% by weight a flow agent of the total weight of the composition; to form a blended powder or uniform mixture with a flow agent.
b) sifting the blended powder o form a powder with a particle size about 100 to 1,000 micrometer.

DETAILED DESCRIPTION OF THE FIGURES

DETAILED DESCRIPTION

For the Summary, Description and Claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

In carrying out particular embodiments provided herein, a plasmolysed micro-organism is selected from the group consisting of fungi, a bacteria, algae, protozoa, or mixtures of two or more of these. In a particular embodiment the micro-organism is a fungus or a bacterium, more particularly it may comprise a yeast.

The micro-organism may be pre-treated to increase its permeability or to remove undesired odors or aromas. Such pre-treatments are disclosed in U.S. Pat. No. 5,521,089, col. 2, line 58 to col. 4, line 63 and WO 93/11869. Peroxygen bleaching of micro-organisms for removing odor and lightening the color of micro-organisms is disclosed. A micro-organism that has at least a part of its endogenous intracellular material removed is defined herein as a "plasmolysed micro-organism."

In one embodiment provided herein is a composition comprising a plasmolyzed micro-organism wherein the plasmolysed micro-organism is from about 25% up to about 60%, by weight, of the total weight of the composition.

In one embodiment provided herein is a composition comprising a plasmolyzed micro-organism wherein the plasmolysed micro-organism is from about 30% up to about 40%, by weight, of the total weight of the composition.

In one embodiment provided herein is a composition comprising a plasmolyzed microorganisms wherein the plasmolysed micro-organism is from about 30% up to about 35%, by weight, of the total weight of the composition.

In one embodiment provided herein is a composition comprising a plasmolyzed microorganism of about 50%, by weight, of the total weight of the composition.

In one embodiment, the desiccant is provided in an amount of from about 10% by weight, of the total weight of the composition.

In one embodiment, the water is provided in an amount of from about 8%, by weight, of the total weight of the composition.

In one embodiment, the mean particle size of the ranges from about 100 up to about 600 micrometers, more particularly from about 200 up to about 600, even more particularly about 300 to about 600 and most particularly about 450 and even more particularly about 200 micrometers.

In one embodiment a plated yeast composition is formed when the yeast cake is poured into a desiccant forming a uniform mixture and then the mixture is sifted The word "desiccant" means a material that adsorbs water from the yeast cake. Particular materials or compounds comprise that may be used as a desiccant are selected from the group consisting of flour, starch, maltodextrin, modified starch, microcrystalline cellulose, cellulose derivative such as methylcellulose, carboxymethylcellulose, hydroxy propyl methyl cellulose, Hydroxy propyl cellulose, cellulose acetate, agar, carrageenan, xanthan gum, gellan gum, galactomannans, gum arabic, pectin, konjac mannan, locust bean gum, curdlan, alginate, inulin, soybean polysaccharide, chitosan, gelatin, milk protein, soybean protein, pea protein, polyethyleneimine, polyacrylamide, polyacrylic acid, polyvinylpyrrolidone, polyvinyl alcohol, polyethylene glycol, silica, calcium carbonate, hydroxylapatite, kaoline, chitin, various salts particles, various inorganic acids powder, and molecular sieve. A particular compound is selected from flour, maltodextrin and starch.

In one embodiment provided herein is a flow agent is provided in an amount of about 1% by weight, of the total weight of the blended powder.

A flow agent is selected to assist in the sifting to allow for ease of sifting. Particular agents in include silica, phosphate salt, magnesium stearate and calcium stearate, more particularly silica.

The dry particles provided herein may be suitable for conveying flavors to beverages, fluid dairy products, condiments, baked goods, frostings, bakery fillings, candy, chewing gum and other food products.

By "flavor or flavoring composition", it is meant here a flavoring ingredient or a mixture of flavoring ingredients, solvents or adjuvants of current use for the preparation of a flavoring formulation, i.e. a particular mixture of ingredients which is intended to be added to an edible composition or chewable product to impart, improve or modify its organoleptic properties, in particular its flavor and/or taste. Flavoring ingredients are well known to a person skilled in the art and their nature does not warrant a detailed description here, which in any case would not be exhaustive, the skilled flavorist being able to select them on the basis of his general knowledge and according to the intended use or application and the organoleptic effect it is desired to achieve. Many of these flavoring ingredients are listed in reference texts such as in the book by S. Arctander, Perfume and Flavor Chemicals, 1969, Montclair, N.J., USA, or its more recent versions, or in other works of similar nature such as Fenaroli's Handbook of Flavor Ingredients, 1975, CRC Press or Synthetic Food Adjuncts, 1947, by M. B. Jacobs, van Nostrand Co., Inc. Solvents and adjuvants of current use for the preparation of a flavoring formulation are also well known in the art.

In a particular embodiment, the flavor is limonene flavor.
In a another embodiment, the flavor is a lemon flavor.
In another embodiment, the flavor is berry flavour.
In another embodiment, the flavor is peppermint flavor.
In another embodiment, the flavor is garlic flavor.

In another embodiment, the flavor is a menthol flavour, more particularly menthol.

Flavors that are derived from or based on fruits where citric acid is the predominant, naturally-occurring acid include but are not limited to, for example, citrus fruits (e.g. lemon, lime), limonene, strawberry, orange, and pineapple. In one embodiment, the flavors is lemon, lime or orange juice extracted directly from the fruit.

Further embodiments of the flavor comprise the juice or liquid extracted from oranges, lemons, grapefruits, key limes, citrons, clementines, mandarins, tangerines, and any other citrus fruit, or variation or hybrid thereof. In a particular embodiment, the flavor comprises a liquid extracted or distilled from oranges, lemons, grapefruits, key limes, citrons, clementines, mandarins, tangerines, any other citrus fruit or variation or hybrid thereof, pomegranates, kiwifruits, watermelons, apples, bananas, blueberries, melons, ginger, bell peppers, cucumbers, passion fruits, mangos, pears, tomatoes, and strawberries.

In a particular embodiment, the flavor comprises a composition that comprises limonene, in a particular embodiment, the composition is a citrus that further comprises limonene.

In another particular embodiment, the flavor comprises a flavor selected from the group comprising strawberry, orange, lime, tropical, berry mix, and pineapple.

The phrase flavor includes not only flavors that impart or modify the smell of foods but include taste imparting or modifying ingredients. The latter do not necessarily have a taste or smell themselves but are capable of modifying the taste that other ingredients provides, for instance, salt enhancing ingredients, sweetness enhancing ingredients, umami enhancing ingredients, bitterness blocking ingredients and so on.

In a further embodiment, suitable sweetening components may be included in the particles described herein. In a particular embodiment, a sweetening component is selected from the group consisting of sugar (e.g., but not limited to sucrose), a *stevia* component (such as but not limited to stevioside or rebaudioside A), sodium cyclamate, aspartame, sucralose, sodium saccharine, and Acesulfam K or mixtures thereof.

The dry particles provided herein may be suitable for conveying flavors to beverages, fluid dairy products, condiments, baked goods, fried goods, frostings, bakery fillings, candy, chewing gum and other food products.

Beverages include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra high temperature, ohmic heating or commercial aseptic sterilization) and hot-filled packaging; and cold-filled products made through filtration or other preservation techniques.

Fluid dairy products include, without limitation, non-frozen, partially frozen and frozen fluid dairy products such as, for example, milks, ice creams, sorbets and yogurts.

Condiments include, without limitation, ketchup, mayonnaise, salad dressing, Worcestershire sauce, fruit-flavored sauce, chocolate sauce, tomato sauce, chili sauce, and mustard.

Baked goods include, without limitation, cakes, cookies, pastries, breads, donuts and the like.

Bakery fillings include, without limitation, low or neutral pH fillings, high, medium or low solids fillings, fruit or milk based (pudding type or mousse type) fillings, hot or cold make-up fillings and nonfat to full-fat fillings.

In one embodiment, the encapsulated flavors provide an initial burst of flavor followed by a sustained release of the flavors.

Particular fragrances that may be used herein are selected from the group consisting of 1-Pentyl-2-propenyl acetate, Hexylcinnamic aldehyde, 8,12-epoxy-13,14,15,16-tetranorlabdane, Tricyclo[5.2.1.0(2,6)]dec-3,4-en-1-yl acetate, Coumarine, 2-Pentyl-1-cyclopentanol, Cyclamen aldehyde, α-Damascone, Dihydromyrcenol, pentadecenolide, methyl ionone, Lilial®, Linalol, cis-4-(1,1-dimethyl)-1-cyclohexyl acetate, 3-methyl-(4,5)-cyclopentadecen-1-one, Tetrahydro-2-isobutyl-4-methyl-4(2H)-pyranol, γ-methyl-benzene pentanol, Hexyl salicylate, and Vertofix Coeur.

In another embodiment provided herein is a compound selected from the group consisting of a) a compound selected from the group consisting of:
3,4-methylenedioxycinnamic acid, N,N-diphenylamide;
N-(1H-pyrazol-5-yl)-N-(thiophen-2-ylmethyl)-2-(p-tolyloxy)acetamide;
N-ethyl-N-(thiophen-2-ylmethyl)-2-(p-tolyloxy)acetamide;
2-(2,3-dihydro-1H-inden-5-yloxy)-N-(1H-pyrazol-3-yl)-N-(thiophen-2-ylmethyl)acetamide;
2-(2,3-dihydro-1H-inden-5-yloxy)-N-(1H-pyrazol-5-yl)-N-(thiophen-2-ylmethyl)acetamide;
2-(2,3-dihydro-1H-inden-5-yloxy)-N-(4-methyl-1H-pyrazol-3-yl)-N-(thiophen-2-ylmethyl)acetamide;
2-(2,3-dihydro-1H-inden-5-yloxy)-N-(1H-pyrazol-4-yl)-N-(thiophen-2-ylmethyl)acetamide;
N-(oxazol-2-yl)-N-(thiophen-2-ylmethyl)-2-(p-tolyloxy)acetamide;
2-(2,3-dihydro-1H-inden-5-yloxy)-N-(3,5-dimethyl-1H-pyrazol-4-yl)-N-(thiophen-2-ylmethyl)acetamide;
N-(3,5-dimethyl-1H-pyrazol-4-yl)-N-(thiophen-2-ylmethyl)-2-(p-tolyloxy)acetamide;
N-(3-methyl-1H-pyrazol-4-yl)-N-(thiophen-2-ylmethyl)-2-(p-tolyloxy)acetamide;
2-(benzo[d] [1,3]dioxol-5-yloxy)-N-(1H-pyrazol-5-yl)-N-(thiophen-2-ylmethyl)acetamide;
2-(benzo[d][1,3]dioxol-5-yloxy)-N-(3,5-dimethyl-1H-pyrazol-4-yl)-N-(thiophen-2-ylmethyl)acetamide;
4-(N-(thiophen-2-ylmethyl)-2-(p-tolyloxy)acetamido)-1H-pyrazol-2-ium chloride;
N-(1H-pyrazol-4-yl)-N-(thiophen-2-ylmethyl)-2-(p-tolyloxy)acetamide;
N-(isoxazol-3-yl)-N-(thiophen-2-ylmethyl)-2-(p-tolyloxy)acetamide;
N-(1-(cyanomethyl)-1H-pyrazol-3-yl)-N-(thiophen-2-ylmethyl)-2-(p-tolyloxy)acetamide;
2-(benzo[d] [1,3]dioxol-5-yloxy)-N-(3-methyl-1H-pyrazol-4-yl)-N-(thiophen-2-ylmethyl)acetamide;
2-(benzo[d] [1,3]dioxol-5-yloxy)-N-(1H-pyrazol-4-yl)-N-(thiophen-2-ylmethyl)acetamide;
N-cyclopropyl-N-(thiophen-2-ylmethyl)-2-(p-tolyloxy)acetamide;
N-allyl-N-(thiophen-2-ylmethyl)-2-(p-tolyloxy)acetamide;
N-(1H-pyrazol-4-yl)-N-(thiophen-2-ylmethyl)-3-p-tolylpropanamide;
2-(4-methoxyphenoxy)-N-(1H-pyrazol-4-yl)-N-(thiophen-2-ylmethyl)acetamide;
N-propyl-N-(thiophen-2-ylmethyl)-2-(p-tolyloxy)acetamide;
N-allyl-2-(benzo[d][1,3]dioxol-5-yloxy)-N-(thiophen-2-ylmethyl)acetamide;
2-(2,3-dihydro-1H-inden-5-yloxy)-N-(pyridin-3-yl)-N-(thiophen-2-ylmethyl)acetamide;
2-(3-methoxyphenoxy)-N-(1H-pyrazol-4-yl)-N-(thiophen-2-ylmethyl)acetamide;
N-(pyridin-4-yl)-N-(thiophen-2-ylmethyl)-2-(p-tolyloxy)acetamide;
N-isopropyl-N-(thiophen-2-ylmethyl)-2-(p-tolyloxy)acetamide;
N-(bicyclo[2.2.1] heptan-2-ylmethyl)-N-(1H-pyrazol-3-yl)-2-(p-tolyloxy)acetamide;
N-ethyl-N-(thiophen-3-ylmethyl)-2-(p-tolyloxy)acetamide;
2-phenoxy-N-phenyl-N-(thiophen-2-ylmethyl)acetamide;
2-(2,3-dihydro-1H-inden-5-yloxy)-N-phenyl-N-(thiophen-2-ylmethyl) acetamide;
N-(bicyclo[2.2.1] heptan-2-ylmethyl)-3-phenyl-N-(1H-pyrazol-3-yl) propanamide;
N-(pyridin-3-yl)-N-(thiophen-2-ylmethyl)-2-(p-tolyloxy)acetamide;
N-ethyl-N-((5-methylthiophen-2-yl)methyl)-2-(p-tolyloxy)acetamide; Example 54.
N 2-(4-ethylphenoxy)-N-(pyridin-3-yl)-N-(thiophen-2-ylmethyl)acetamide;
N-(1-methyl-1H-pyrazol-5-yl)-N-(thiophen-2-ylmethyl)-2-(p-tolyloxy)acetamide;
N-(bicyclo[2.2.1]heptan-2-ylmethyl)-2-phenoxy-N-(1H-pyrazol-3-yl)acetamide;
2-(benzo[d] [1,3]dioxol-5-yloxy)-N-(pyridin-3-yl)-N-(thiophen-2-ylmethyl)acetamide;
N-ethyl-2-(4-fluorophenoxy)-N-(thiophen-2-ylmethyl)acetamide;
N-sec-butyl-N-(thiophen-2-ylmethyl)-2-(p-tolyloxy)acetamide;
2-(4-chlorophenoxy)-N-phenyl-N-(thiophen-2-ylmethyl)acetamide;
N-phenyl-N-(thiazol-2-ylmethyl)-2-(p-tolyloxy)acetamide;
N-methyl-N-(thiophen-2-ylmethyl)-2-(p-tolyloxy)acetamide;
3-(2-(3-methoxyphenoxy)-N-(thiophen-2-ylmethyl)acetamido)pyridinium chloride;
2-(3-methoxyphenoxy)-N-(pyridin-2-yl)-N-(thiophen-2-ylmethyl)acetamide;
2-(2-isopropyl-5-methylphenoxy)-N-(1H-pyrazol-3-yl)-N-(thiophen-2-ylmethyl)acetamide;
N-((5-methylthiophen-2-yl)methyl)-N-phenyl-2-(p-tolyloxy)acetamide;
N-(pyridin-2-yl)-N-(thiophen-2-ylmethyl)-2-(m-tolyloxy)acetamide;
N-(pyridin-3-yl)-N-(thiophen-2-ylmethyl)-2-(m-tolyloxy)acetamide;
2-(3,4-dimethylphenoxy)-N-(pyridin-2-yl)-N-(thiophen-2-ylmethyl)acetamide;
2-(4-ethylphenoxy)-N-(pyridin-2-yl)-N-(thiophen-2-ylmethyl)acetamide;
2-(3-methoxyphenoxy)-N-(pyridin-3-yl)-N-(thiophen-2-ylmethyl)acetamide;
N-ethyl-3-phenyl-N-(thiophen-2-ylmethyl)propanamide;
N-ethyl-N-(thiazol-5-ylmethyl)-2-(p-tolyloxy)acetamide;
(R)—N-(3-methylbutan-2-yl)-2-(3-nitrophenoxy)acetamide;
N-ethyl-2-phenoxy-N-(thiophen-2-ylmethyl)acetamide;

((R)—N-(1-hydroxy-3-methylbutan-2-yl)-N-isopropyl-2-(m-tolyloxy)acetamide;
N-(4-fluorophenyl)-N-(thiophen-2-ylmethyl)-2-(p-tolyloxy)acetamide;
2 3,4,6-trimethyl-N-(pyridin-2-yl)-N-(thiophen-2-ylmethyl)benzofuran-2-carboxamide;
2-(4-methoxyphenoxy)-N-(pyridin-3-yl)-N-(thiophen-2-ylmethyl)acetamide;
3,5-dimethyl-N-(pyridin-2-yl)-N-(thiophen-2-ylmethyl)benzofuran-2-carboxamide;
2-(3-methoxyphenoxy)-N-(pyridin-2-yl)-N-(thiophen-2-ylmethyl)acetamide;
N-allyl-2-(2-hydroxyphenoxy)-N-((5-methylthiophen-2-yl)methyl)acetamide;
N-(pyrazin-2-yl)-N-(thiophen-2-ylmethyl)-2-(p-tolyloxy)acetamide;
2-(4-isopropylphenoxy)-N-(pyridin-2-yl)-N-(thiophen-2-ylmethyl)acetamide;
2-(4-fluorophenoxy)-N-(pyridin-3-yl)-N-(thiophen-2-ylmethyl)acetamide;
N-benzyl-N-ethyl-2-(p-tolyloxy)acetamide;
2-(4-chlorophenoxy)-N-(pyridin-2-yl)-N-(thiophen-2-ylmethyl)acetamide;
2-(4-bromophenoxy)-N-(pyridin-2-yl)-N-(thiophen-2-ylmethyl)acetamide;
N-(2-chlorophenyl)-N-(thiophen-2-ylmethyl)-2-(p-tolyloxy)acetamide;
2-(2-isopropyl-5-methylcyclohexyloxy)-N-(2-(pyridin-4-yl)ethyl)acetamide;
N-(thiazol-2-yl)-N-(thiophen-2-ylmethyl)-2-(p-tolyloxy)acetamide;
N-(cyclohexylmethyl)-2-(2,4-dimethylphenoxy)-N-(pyridin-2-yl)acetamide;
N-(furan-2-ylmethyl)-N-(pyridin-2-yl)-2-(p-tolyloxy)acetamide;
3,6-dimethyl-N-(pyridin-2-yl)-N-(thiophen-2-ylmethyl)benzofuran-2-carboxamide;
2-(3-fluorophenoxy)-N-(pyridin-3-yl)-N-(thiophen-2-ylmethyl)acetamide;
N-ethyl-N-(thiazol-2-ylmethyl)-2-(p-tolyloxy)acetamide;
N-ethyl-N-(3-fluorobenzyl)-2-(p-tolyloxy)acetamide;
3,5,6-trimethyl-N-(pyridin-2-yl)-N-(thiophen-2-ylmethyl)benzofuran-2-carboxamide;
N-((5-ethylthiophen-2-yl)methyl)-N-phenyl-2-(p-tolyloxy)acetamide;
N-((5-ethylthiophen-2-yl)methyl)-N-phenyl-2-(p-tolyloxy)acetamide;
N-(pyrimidin-2-yl)-N-(thiophen-2-ylmethyl)-2-(p-tolyloxy)acetamide;
2-phenoxy-N-(pyridin-3-yl)-N-(thiophen-2-ylmethyl)acetamide;
2-(4-fluorophenoxy)-N-(pyridin-2-yl)-N-(thiophen-2-ylmethyl)acetamide;
N-(thiophen-2-ylmethyl)butan-1-amine;
2-(3-chlorophenoxy)-N-(pyridin-2-yl)-N-(thiophen-2-ylmethyl)acetamide;
N-((3-methylthiophen-2-yl)methyl)-N-phenyl-2-(p-tolyloxy)acetamide:
2-phenoxy-N-(pyridin-2-yl)-N-(thiophen-2-ylmethyl)acetamide:
(E)-3-(benzo[d] [1,3]dioxol-5-yl)-N-(1H-pyrazol-5-yl)-N-(thiophen-2-ylmethyl)acrylamide;
(E)-N-(5-methyl-1H-pyrazol-4-yl)-N-(thiophen-2-ylmethyl)-3-p-tolylacrylamide;
(E)-N-(1H-pyrazol-5-yl)-N-(thiophen-2-ylmethyl)-3-p-tolylacrylamide;
(E)-N-(1H-pyrazol-4-yl)-N-(thiophen-2-ylmethyl)-3-p-tolylacrylamide;
(E)-3-p-tolylacryloyl chloride.
N-(thiophen-2-ylmethyl)-1H-pyrazol-4-amine.
E)-3-(benzo[d][1,3]dioxol-5-yl)-N-(1H-pyrazol-4-yl)-N-(thiophen-2-ylmethyl)acrylamide
(E)-N-(3,5-dimethyl-1H-pyrazol-4-yl)-N-(thiophen-2-ylmethyl)-3-p-tolylacrylamide;
(E)-3-(benzo[d][1,3]dioxol-5-yl)-N-(5-methyl-1H-pyrazol-4-yl)-N-(thiophen-2-ylmethyl)acrylamide;
(E)-3-(benzo[d][1,3]dioxol-5-yl)-N-cyclopropyl-N-(thiophen-2-ylmethyl)acrylamide;
E)-3-(benzo[d] [1,3]dioxol-5-yl)-N-ethyl-N-(thiophen-2-ylmethyl)acrylamide;
(E)-3-(benzo[d][1,3]dioxol-5-yl)-N-(3,5-dimethyl-1H-pyrazol-4-yl)-N-(thiophen-2-ylmethyl)acrylamide;
(E)-N-ethyl-N-(thiophen-2-ylmethyl)-3-p-tolylacrylamide;
(E)-3-(4-methoxyphenyl)-N-(1H-pyrazol-4-yl)-N-(thiophen-2-ylmethyl)acrylamide;
(E)-3-(4-methoxyphenyl)-N-(1H-pyrazol-5-yl)-N-(thiophen-2-ylmethyl)acrylamide;
N-(1H-pyrazol-5-yl)-N-(thiophen-2-ylmethyl)-3-p-tolylpropanamide;
N-(3,5-dimethyl-1H-pyrazol-4-yl)-N-(thiophen-2-ylmethyl)cinnamamide;
N-(1H-pyrazol-5-yl)-N-(thiophen-2-ylmethyl)cinnamamide;
N-(1H-pyrazol-4-yl)-N-(thiophen-2-ylmethyl)cinnamamide;
(E)-3-(2,3-dihydro-1H-inden-5-yl)-N-(3,5-dimethyl-1H-pyrazol-4-yl)-N(thiophen-2-ylmethyl) acrylamide;
((E)-3-(benzo[d][1,3]dioxol-5-yl)-N-(pyridin-3-yl)-N-(thiophen-2-ylmethyl)acrylamide;
(+/−) (E)-2-phenyl-N-(1H-pyrazol-4-yl)-N-(thiophen-2-ylmethyl)cyclopropanecarboxamide
(E)-3-(benzo[d] [1,3]dioxol-5-yl)-N-(pyridin-2-yl)-N-(thiophen-2-ylmethyl)acrylamide;
2-phenoxy-N-(1H-pyrazol-5-yl)-N-(thiophen-2-ylmethyl)acetamide;
(E)-3-(2,3-dihydro-1H-inden-5-yl)-N-(1H-pyrazol-5-yl)-N-(thiophen-2-ylmethyl) Acrylamide
(E)-3-(2,3-dihydro-1H-inden-5-yl)-N-(5-methyl-1H-pyrazol-4-yl)-N-(thiophen-2-ylmethyl) acrylamide;
N-(bicyclo[2.2.1] heptan-2-yl)-N-(1H-pyrazol-5-yl)cinnamamide;
N-ethyl-N-(thiophen-2-ylmethyl)cinnamamide;
2-(2,3-dihydro-1H-inden-5-yloxy)-N-ethyl-N-(thiazol-5-ylmethyl)acetamide;
2-(2,3-dihydro-1H-inden-5-yloxy)-N-ethyl-N-(thiazol-5-ylmethyl)acetamide;
2-(benzo[d] [1,3]dioxol-5-yloxy)-N-phenyl-N-(thiophen-2-ylmethyl)acetamide;
N-allyl-N-(thiophen-2-ylmethyl)cinnamamide;
(+/−) (E)-N-ethyl-2-phenyl-N-(thiophen-2-ylmethyl)cyclopropanecarboxamide;
(E)-N-(bicyclo[2.2.1] heptan-2-yl)-N-(1H-pyrazol-5-yl)-3-p-tolylacrylamide;
N-(bicyclo[2.2.1] heptan-2-yl)-2-(2,3-dihydro-1H-inden-5-yloxy)-N-(1H-pyrazol-5-yl) acetamide;
N-(bicyclo[2.2.1] hept-5-en-2-ylmethyl)-N-(1H-pyrazol-5-yl)-2-(p-tolyloxy)acetamide;
2-(cyclohexyloxy)-N-(1H-pyrazol-5-yl)-N-(thiophen-2-ylmethyl)acetamide;
N-(bicyclo[2.2.1] heptan-2-yl)-2-(cyclohexyloxy)-N-(1H-pyrazol-5-yl)acetamide;
3,4,6-trimethyl-N-(pyridin-2-yl)-N-(thiophen-2-ylmethyl)benzofuran-2-carboxamide;

2-(2,3-dihydro-1H-inden-5-yloxy)-N-ethyl-N-((5-methylthiophen-2-yl)methyl)acetamide;
(E)-N-phenyl-N-(thiophen-2-ylmethyl)-3-p-tolylacrylamide;
N-phenyl-N-(thiophen-2-ylmethyl)cinnamamide;
N-(pyridin-2-yl)-N-(thiophen-2-ylmethyl)cinnamamide;
(+/−) (E)-N,2-diphenyl-N-(thiophen-2-ylmethyl)cyclopropanecarboxamide;
3,5-dimethyl-N-(pyridin-2-yl)-N-(thiophen-2-ylmethyl)benzofuran-2-carboxamide;
N-(bicyclo[2.2.1] heptan-2-yl)-N-(1H-pyrazol-5-yl)-3-p-tolylpropanamide;
(E)-N-allyl-3-(7-chloro benzo[d][1,3]dioxol-5-yl)-N-(thiophen-2-ylmethyl)acrylamide;
N-(pyridin-3-yl)-N-(thiophen-2-ylmethyl)cinnamamide;
3,6-dimethyl-N-(pyridin-2-yl)-N-(thiophen-2-ylmethyl)benzofuran-2-carboxamide;
(E)-3-(benzo[d][1,3]dioxol-5-yl)-N,N-bis(thiophen-2-ylmethyl)acrylamide;
2-(benzo[d] [1,3]dioxol-5-yloxy)-N-phenyl-N-(thiophen-2-ylmethyl)acetamide;
2-(2,3-dihydro-1H-inden-5-yloxy)-N-ethyl-N-(thiophen-2-ylmethyl)acetamide;
2-(2-hydroxy-4-methylphenoxy)-N-(1H-pyrazol-5-yl)-N-(thiophen-2-ylmethyl)acetamide;
N-ethyl-2-(2-hydroxy-4-methylphenoxy)-N-(thiophen-2-ylmethyl)acetamide;
N-phenyl-N-(thiophen-2-ylmethyl)-2-(p-tolyloxy)acetamide;
2-(2,3-dihydrobenzo[b] [1,4] dioxin-6-yloxy)-N-phenyl-N-(thiophen-2-ylmethyl)acetamide;
2-(3-methoxyphenoxy)-N-phenyl-N-(thiophen-2-ylmethyl)acetamide;
2-(4-methoxyphenoxy)-N-phenyl-N-(thiophen-2-ylmethyl)acetamide;
2-(4-fluorophenoxy)-N-phenyl-N-(thiophen-2-ylmethyl)acetamide;
2-(benzo[d] [1,3]dioxol-5-yloxy)-N-ethyl-N-(thiophen-2-ylmethyl)acetamide;
N-ethyl-2-(3-methoxyphenoxy)-N-(thiophen-2-ylmethyl)acetamide;
N-phenyl-N-(thiophen-2-ylmethyl)-2-(m-tolyloxy)acetamide;
N-ethyl-N-(furan-3-ylmethyl)-2-(p-tolyloxy)acetamide;
N-ethyl-2-(4-methoxyphenoxy)-N-(thiophen-2-ylmethyl)acetamide;
N-ethyl-N-(thiophen-2-ylmethyl)-2-(o-tolyloxy)acetamide;
2-(3-fluorophenoxy)-N-phenyl-N-(thiophen-2-ylmethyl)acetamide;
2-(benzo[d][1,3]dioxol-5-yloxy)-N-ethyl-N-(furan-3-ylmethyl)acetamide;
N-ethyl-3-(4-methoxyphenyl)-N-(thiophen-2-ylmethyl)propanamide;
N-ethyl-N-(thiophen-2-ylmethyl)-2-(m-tolyloxy)acetamide;
N-(pyridin-2-yl)-N-(thiophen-2-ylmethyl)-2-(p-tolyloxy)acetamide;
N-ethyl-2-(2-hydroxyphenoxy)-N-(thiophen-2-ylmethyl)acetamide;
2-(4-ethylphenoxy)-N-phenyl-N-(thiophen-2-ylmethyl)acetamide;
2-(3,4-dimethylphenoxy)-N-phenyl-N-(thiophen-2-ylmethyl)acetamide;
2-(benzo[d] [1,3]dioxol-5-yloxy)-N-(pyridin-2-yl)-N-(thiophen-2-ylmethyl)acetamide;
2-(3-chlorophenoxy)-N-phenyl-N-(thiophen-2-ylmethyl)acetamide;
N-ethyl-3-(4-fluorophenyl)-N-(thiophen-2-ylmethyl)propanamide;
2-(2-hydroxyphenoxy)-N-phenyl-N-(thiophen-2-ylmethyl)acetamide;
N-(pyridin-2-yl)-N-(thiophen-2-ylmethyl)-2-(p-tolyloxy)acetamide;
N-ethyl-N-(furan-2-ylmethyl)-2-(p-tolyloxy)acetamide;
N-ethyl-N-(thiophen-2-ylmethyl)-3-o-tolylpropanamide;
2-(2-fluorophenoxy)-N-phenyl-N-(thiophen-2-ylmethyl)acetamide;
N-phenyl-N-(thiophen-2-ylmethyl)-2-(o-tolyloxy)acetamide;
N-ethyl-2-(3-fluorophenoxy)-N-(thiophen-2-ylmethyl)acetamide;
2-(benzo[d] [1,3]dioxol-5-yloxy)-N-ethyl-N-(furan-2-ylmethyl)acetamide;
2-(2-chlorophenoxy)-N-phenyl-N-(thiophen-2-ylmethyl)acetamide;
2-(4-isopropylphenoxy)-N-phenyl-N-(thiophen-2-ylmethyl)acetamide;
N-benzyl-N-phenyl-2-(p-tolyloxy)acetamide;
N-ethyl-3-(3-fluorophenyl)-N-(thiophen-2-ylmethyl)propanamide;
N-(pyridin-2-yl)-N-(thiophen-2-ylmethyl)-2-(p-tolyloxy)propanamide;
N-ethyl-N-(thiophen-2-ylmethyl)-2-(p-tolyloxy)propanamide;
N-benzyl-N-phenyl-2-(p-tolyloxy)acetamide;
N-ethyl-3-(3-fluorophenyl)-N-(thiophen-2-ylmethyl)propanamide;
N-ethyl-N-(thiophen-2-ylmethyl)-3-m-tolylpropanamide;
N-phenyl-N-(thiophen-2-ylmethyl)benzofuran-2-carboxamide;
N-ethyl-N-(thiophen-2-ylmethyl)benzofuran-2-carboxamide;
2-(4-cyanophenoxy)-N-ethyl-N-(thiophen-2-ylmethyl)acetamide;
N-(1-methyl-1H-imidazol-2-yl)-N-(thiophen-2-ylmethyl)-2-(p-tolyloxy)acetamide;
N-ethyl-3-(4-methoxyphenyl)-N-(thiophen-2-ylmethyl)propanamide;
N-ethyl-2-(2-fluorophenoxy)-N-(thiophen-2-ylmethyl)acetamide;
2-(4-(hydroxymethyl)phenoxy)-N-phenyl-N-(thiophen-2-ylmethyl)acetamide;
N-cyclohexyl-N-phenyl-2-(p-tolyloxy)acetamide;
2-(6-methyl-4-oxo-4H-chromen-2-yloxy)-N-phenyl-N-(thiophen-2-ylmethyl)acetamide;
N-ethyl-3-(4-oxo-3,4-dihydroquinazolin-2-yl)-N-(thiophen-2-ylmethyl)propanamide;
2-(4-hydroxyphenoxy)-N-phenyl-N-(thiophen-2-ylmethyl)acetamide;
2-(4-cyanophenoxy)-N-phenyl-N-(thiophen-2-ylmethyl)acetamide;
N-propyl-N-(thiophen-2-ylmethyl)-2-(p-tolyloxy)acetamide;
N-(pyridin-2-yl)-N-(thiophen-2-ylmethyl)-3-p-tolylpropanamide;
2-(benzyloxy)-N-phenyl-N-(thiophen-2-ylmethyl)acetamide;
N-phenyl-N-(pyridin-4-ylmethyl)-2-(p-tolyloxy)acetamide;
N-ethyl-2-methyl-N-(thiophen-2-ylmethyl)-2-(p-tolyloxy)propanamide;
N-phenyl-N-(pyridin-4-ylmethyl)-2-(p-tolyloxy)acetamide;
N-ethyl-2-methyl-N-(thiophen-2-ylmethyl)-2-(p-tolyloxy)propanamide;

2-(2-hydroxy-4-methylphenoxy)-N-(1H-pyrazol-4-yl)-N-(thiophen-2-ylmethyl)acetamide;
(E)-N-ethyl-3-(4-methoxyphenyl)-N-(thiophen-2-ylmethyl)acrylamide;
(E)-N-ethyl-N-(furan-3-ylmethyl)-3-p-tolyl acrylamide;
(E)-N-ethyl-N-(thiophen-2-ylmethyl)-3-o-tolylacrylamide;
(E)-3-(benzo[d][1,3]dioxol-5-yl)-N-ethyl-N-(furan-3-ylmethyl)acrylamide;
(E)-3-(2,3-dihydrobenzofuran-5-yl)-N-ethyl-N-(thiophen-2-ylmethyl)acrylamide
(E)-3-(2,3-dihydrobenzo[b] [1,4] dioxin-6-yl)-N-ethyl-N-(thiophen-2-25 ylmethyl)acrylamide;
N-ethyl-5-methyl-N-(thiophen-2-ylmethyl)benzofuran-2-carboxamide;
N-ethyl-N-(thiophen-2-ylmethyl)-3-p-tolylpropanamide;
(E)-N-ethyl-3-(4-fluorophenyl)-N-(thiophen-2-ylmethyl)acrylamide;
(E)-3-(2,3-dihydro-1H-inden-5-yl)-N-ethyl-N-(furan-3-ylmethyl)acrylamide;
(E)-N-ethyl-3-(5-methylthiophen-2-yl)-N-(thiophen-2-ylmethyl)acrylamide;
(E)-3-(benzo[d][1,3]dioxol-5-yl)-N-ethyl-N-(furan-2-ylmethyl)acrylamide;
(E)-3-(2,3-dihydro-1H-inden-5-yl)-N-ethyl-N-(thiophen-2-ylmethyl)acrylamide;
(E)-N-ethyl-3-(3-hydroxy-4-methoxyphenyl)-N-(thiophen-2-ylmethyl)acrylamide;
(E)-N-ethyl-N-(furan-2-ylmethyl)-3-p-tolylacrylamide;
(E)-N-ethyl-3-(2-fluorophenyl)-N-(thiophen-2-ylmethyl)acrylamide;
(E)-N-ethyl-N-(thiophen-2-ylmethyl)-3-m-tolylacrylamide;
(E)-N-ethyl-3-(3-methoxyphenyl)-N-(thiophen-2-ylmethyl)acrylamide;
(E)-3-(2,2-difluorobenzo[d] [1,3]dioxol-5-yl)-N-ethyl-N-(thiophen-2-ylmethyl)acrylamide
(E)-N-ethyl-3-(3-fluorophenyl)-N-(thiophen-2-ylmethyl)acrylamide
(E)-N-ethyl-3-(5-methylfuran-2-yl)-N-(thiophen-2-ylmethyl)acrylamide
(E)-3-(4-cyanophenyl)-N-ethyl-N-(thiophen-2-ylmethyl)acrylamide
E)-N-ethyl-3-(thiophen-2-yl)-N-(thiophen-2-ylmethyl)acrylamide;
(E)-3-(2-cyanophenyl)-N-ethyl-N-(thiophen-2-ylmethyl)acrylamide;
(E)-3-(2,3-dihydro-1H-inden-5-yl)-N-ethyl-N-(furan-2-ylmethyl)acrylamide;
3-(2,3-dihydro-1H-inden-5-yl)-N-ethyl-N-(thiophen-2-ylmethyl)propanamide
(E)-N-ethyl-N-(thiophen-2-ylmethyl)-3-(thiophen-3-yl)acrylamide
(E)-3-(3-cyanophenyl)-N-ethyl-N-(thiophen-2-ylmethyl)acrylamide;
(E)-N-ethyl-3-(4-hydroxyphenyl)-N-(thiophen-2-ylmethyl)acrylamide;
(E)-N-ethyl-3-(1-methyl-1H-pyrrol-2-yl)-N-(thiophen-2-ylmethyl)acrylamide;
(E)-N-ethyl-3-(1-methyl-1H-pyrrol-2-yl)-N-(thiophen-2-ylmethyl)acrylamide;
(E)-N-ethyl-3-(2-methoxyphenyl)-N-(thiophen-2-ylmethyl)acrylamide;
(E)-N-ethyl-3-(3-hydroxyphenyl)-N-(thiophene-2-ylmethyl)acrylamide
2-(3-cyanophenoxy)-N-phenyl-N-(thiophen-2-ylmethyl)acetamide;
2-bromo-N-phenyl-N-(thiophen-2-ylmethyl)acetamide;
N-ethyl-2-(2-hydroxy-5-methylphenoxy)-N-(thiophen-2-ylmethyl)acetamide;
N-ethyl-2-(3-fluoro-4-methylphenoxy)-N-(thiophen-2-ylmethyl)acetamide;
2-(3-fluoro-4-methylphenoxy)-N-phenyl-N-(thiophen-2-ylmethyl)acetamide;
2-(4-fluoro-3-methylphenoxy)-N-phenyl-N-(thiophen-2-ylmethyl)acetamide;
2-(5-methylpyridin-2-yloxy)-N-phenyl-N-(thiophen-2-ylmethyl)acetamide;
2-(3-fluoro-4-methoxyphenoxy)-N-phenyl-N-(thiophen-2-ylmethyl)acetamide;
2-(6-methylpyridin-2-yloxy)-N-phenyl-N-(thiophen-2-ylmethyl)acetamide;
2-(6-methylpyridin-3-yloxy)-N-phenyl-N-(thiophen-2-ylmethyl)acetamide;
N-phenyl-N-(thiophen-2-ylmethyl)-2-(4-(trifluoromethyl)phenoxy)acetamide;
N-phenyl-N-(thiophen-2-ylmethyl)-2-(thiophen-2-yloxy)acetamide;
2-(4-allyl-2-methoxyphenoxy)-N-phenyl-N-(thiophen-2-ylmethyl)acetamide;
and b) a compound selected from the group consisting of: WS-23 (2-Isopropyl-N,2,3-trimethylbutyramide), FEMA 3804; WS-3 (N-Ethyl-p-menthane-3-carboxamide), FEMA 3455; WS-5 [Ethyl 3-(p-menthane-3-carboxamido)acetate], FEMA 4309; WS-12 (1R,2S,5R)—N-(4-Methoxyphenyl)-p-menthanecarboxamide, FEMA 4681; WS-27 (N-Ethyl-2, 2-diisopropylbutanamide), FEMA 4557; N-Cyclopropyl-5-methyl-2-isopropylcyclohexanecarboxamide, FEMA 4693, WS-116 (N-(1,1-Dimethyl-2-hydroxyethyl)-2,2-diethylbutanamide), FEMA 4603; Menthoxyethanol, FEMA 4154; N-(4-cyanomethylphenyl)-p-menthanecarboxamide, FEMA 4496; N-(2-(Pyridin-2-yl)ethyl)-3-p-menthanecarboxamide, FEMA 4549; N-(2-Hydroxyethyl)-2-isopropyl-2,3-dimethylbutanamide, FEMA 4602 and (also N-(4-(carbamoylmethyl)phenyl)-menthylcarboxamide, FEMA 4684; (1R,2S,5R)—N-(4-Methoxyphenyl)-p-menthanecarboxamide (WS-12), FEMA 4681; (2S,5R)—N-[4-(2-Amino-2-oxoethyl)phenyl]-p-menthanecarboxamide, FEMA 4684; and N-Cyclopropyl-5-methyl-2-isopropylcyclohexanecarbonecarboxamide, FEMA 4693;2-[(2-p-Menthoxy)ethoxy]ethanol, FEMA 4718, (2,6-Diethyl-5-isopropyl-2-methyltetrahydropyran, FEMA 4680); trans-4-tert-Butylcyclohexanol, FEMA 4724; (−)-Menthol, FEMA 2665; Isopulegol. FEMA 2962; (−)-Menthyl lactate, FEMA 37483;-((−)-Menthoxy)propane-1,2-diol, FEMA 3784; (−)-Menthyl ethylene glycol carbonate, FEMA 3805; (−)-Menthone 1,2-glycerol ketal, FEMA 3807; (racemic)=DL-Menthone 1,2-glycerol ketal, FEMA 3808; (−)-Menthyl succinate, FEMA 3810; (−)-Menthyl 1&2 propylene glycol carbonates, FEMA 3806; (racemic)=DL-Menthyl 1&2 propylene glycol carbonates, FEMA 3992; Menthyl glutarate, FEMA 4006; (+)-cis & (−)-trans p-menthane-3,8-diol, FEMA 4053; Menthyl pyrrolidone carboxylate, FEMA 4155; N,N-Dimethyl (−)-menthyl succinamide, FEMA 4230; (−)-Menthone (S)-lactic acid ketal, FEMA; 4285; (−)-Menthyl (S)-3-hydroxybutyrate, FEMA 4308; (−)-Menthyl acetoacetate FEMA 4327; (1R,2S,5R)—N-(4-(cyanomethyl)phenyl)menthylcarboxamide, FEMA 4496; (−)-Cubebol=(1R,4S,5R,6R,7S,10R)-7-isopropyl-4,10-dimethyl-tricyclo[4.4.0.0(1,5)]decan-4-ol, FEMA 4497; 1R,2S,5R)—N-(2-(pyridin-2-yl)ethyl)menthylcarboxamide, FEMA 4549; N-(2-Hydroxyethyl)-2,3-dimethyl-2-isopropylbutanamide, FEMA 4602; Di-(−)-menthyl glutarate, FEMA 4604; (1R,2S,5R)—N-(4-(carbamoylmethyl)phenyl)-menthylcarboxamide, FEMA 4684; 2-[2-(p-menthan-3-yl oxy)ethoxy] ethanol=(1R,2S,5R)-2-[2-(2-Isopropyl-5-methyl-cyclohexyloxy)ethoxy]-ethanol, FEMA 4718; 1R,2R,4R)-1-(2-Hydroxy-4-methylcyclohexyl)ethanone, FEMA 4742; and 2-(p-tolyloxy)-N-(1H-pyrazol-5-yl)-N-((thiophen-2-yl)methyl)acetamide, FEMA 4809. In one embodiment, provided herein is 2-(p-tolyloxy)-N-(1H-pyrazol-5-yl)-N-((thiophen-2-yl)methyl)acetamide. The following examples are illustrative only and are not meant to limit the scope of the claims, the summary or any invention presented herein.

EXAMPLES

Examples 1-3

200.1 g plasmolyzed yeast cell was dispersed in 300 g limonene oil. 34.4 g (example 1), 65.4 g (example 2) and 81.5 g (example 3) water were directly poured into 166.7 g yeast/limonene suspension with moderate agitation respectively. The formed 3 yeast cakes were stored at room temperature for 6 days. The maltodextrin 2DE, as desiccant, was dried to constant moisture content (around 4%) in the oven at 100° C. in advance. The above prepared 3 yeast cakes were blended with maltodextrin 2DE in the blender respectively with desiccant/yeast cake mass ratio of 2.5 and additional $SiO_2$ (e.g. 0.8%). The blended mixtures were then sifted through 4 different sieves with mesh size 1700/800/300/100 μm. The following fractions were obtained:

TABLE 1 sifted particles from example 1

| Fraction | % Mass Distribution | % flavor | % water |
|---|---|---|---|
| >1700 μm | 0.5 | 44.7 | 5.6 |
| 800-1700 μm | 13.1 | 46.5 | 5.1 |
| 300-800 μm | 6.1 | 47.9 | 5.3 |
| 100-300 μm | 57.5 | 3.2 | 5.8 |
| <100 μm | 22.8 | 2.4 | 6.1 |

TABLE 2 sifted particles from example 2

| Fraction | % Mass Distribution | % flavor | % water |
|---|---|---|---|
| >1700 μm | 0.3 | 47.8 | 6.4 |
| 800-1700 μm | 12.2 | 50.8 | 6.5 |
| 300-800 μm | 8.5 | 48.9 | 6.7 |
| 100-300 μm | 57.5 | 1.8 | 6.8 |
| <100 μm | 21.5 | 1.6 | 6.8 |

TABLE 3 sifted particles from example 3

| Fraction | % Mass Distribution | % flavor | % water |
|---|---|---|---|
| >1700 μm | 0.2 | 47.8 | 8.0 |
| 800-1700 μm | 13.8 | 52.3 | 7.5 |
| 300-800 μm | 8.7 | 46.7 | 7.8 |
| 100-300 μm | 51.7 | 1.1 | 8.0 |
| <100 μm | 25.6 | 0.2 | 8.2 |

Figure 1:
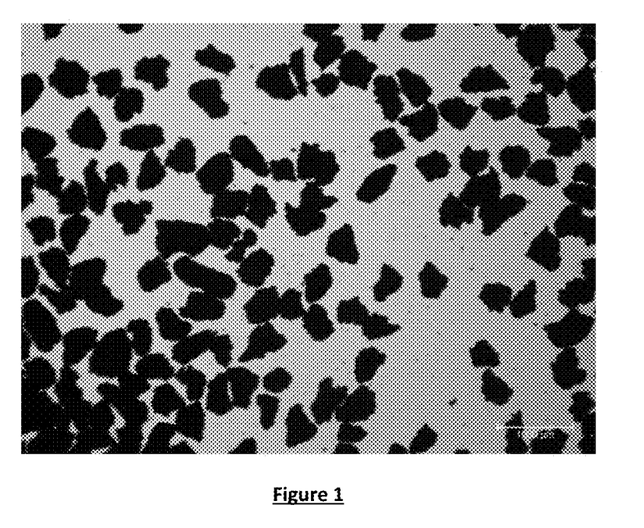
FIG. 1 shows a representative example of the powders generated in Examples 1-3.

The bottom two fraction (<300 μm) being mainly desiccant is considered as a waste product which might be recycled. The fractions above 300-1700 μm gave a very nice, dust free, free-flowing and high-loaded powder (FIG. 1). The content of desiccant left in these powders is quantified to be around 10%. They will be the subject of this invention.

Examples 4-5

133.4 g plasmolyzed yeast cell was dispersed in 200 g limonene oil. 130.8 g water was directly poured into the suspension with moderate agitation. The formed solid yeast cake of 232 g was stored at room temperature for 1 day (sample 4) and 14 days (sample 5) respectively. The maltodextrin 2DE, as desiccant, was dried to constant moisture content (around 4%) in the oven at 80° C. in advance. The above prepared 2 yeast cakes were blended with maltodextrin 2DE in the blender with desiccant/yeast cake mass ratio of 2.5 and additional $SiO_2$ (e.g. 0.8%) respectively. The blended mixtures were then sifted through 2 different sieves with mesh size 1700/800/300/100 μm. The following fractions were obtained:

TABLE 4 sifted particles from example 4

| Fraction | % Mass Distribution | % flavor | % water |
|---|---|---|---|
| >1700 μm | 0.5 | 19.8 | 8.9 |
| 800-1700 μm | 16.1 | 21.1 | 9.2 |
| 300-800 μm | 9.2 | 17.8 | 9.4 |
| 100-300 μm | 51.8 | 10.1 | 8.9 |
| <100 μm | 22.4 | 7.1 | 5.8 |

TABLE 5 sifted particle from example 5

| Fraction | % Mass Distribution | % flavor | % water |
|---|---|---|---|
| >1700 μm | 0.3 | 55.4 | 5.4 |
| 800-1700 μm | 16.3 | 54.7 | 5.5 |
| 300-800 μm | 6.6 | 48.9 | 5.2 |
| 100-300 μm | 54.0 | 2.2 | 5.6 |
| <100 μm | 22.8 | 2.1 | 6.8 |

The bottom two fractions (<300 μm) being mainly desiccant are considered as a waste product which might be recycled. The fractions above 300-1700 μm gave a very nice, dust free, free-flowing powder. The content of desiccant left in these powders is quantified to be around 15% for example 4 and around 10% for example 5. They will be the subject of this invention.

Example 6

66.7 g plasmolyzed yeast cell was dispersed in 100 g limonene oil. And 65.4 g water was directly poured into the suspension with moderate agitation respectively. The formed solid yeast cakes were stored at room temperature for 6 days. AGG maltodextirn 4-8DE, as desiccant was dried to constant moisture content (around 4%) in the oven at 80° C. in advance. The prepared cake was blended with AGG maltodextrin 4-8DE in the blender with desiccant/yeast cake mass ratio of 2.5 and additional $SiO_2$ (e.g. 1%) respectively. The above mixture was then ground in the grinder and sifted through to collected fractions as following:

TABLE 6

| sifted particles from example 6 | | | |
|---|---|---|---|
| Fraction | % Mass Distribution | % flavor | % water |
| >600 μm | 0 | — | — |
| 250-600 μm | 31 | 29 | 5.1 |
| 100-250 μm | 51.8 | 6.5 | 5.3 |
| <100 μm | 17.2 | 4.0 | 5.2 |

The bottom two fractions (<250 μm) being mainly desiccant are considered as a waste product which might be recycled. The fractions above 250-600 μm gave a very nice, dust free, free-flowing and high-loaded powder. The content of desiccant left in these powders is quantified to be around 16%. They will be the subject of this invention.

Example 7

66.7 g plasmolyzed yeast cell was dispersed in 99.8 g limonene oil. And 16.7 g water was directly poured into the suspension with moderate agitation respectively. The formed solid yeast cakes were stored at closed container at 80° C. for 16 h. The wheat flour, as desiccant, was dried to constant moisture content (around 5%) in the oven at 80° C. in advance. The prepared cake was blended with wheat flour in the blender with desiccant/yeast cake mass ratio of 1 and additional $SiO_2$ (e.g. 2%) respectively. The blended mixtures were ground in a ball miller and finally sift the powder to collect the fraction with size above 200 μm. The prepared powders have the size of around average 250 μm, oil loading of around 40% and moisture of 6%. The content of desiccant left in these powders is quantified to be around 15%.

Example 8

66.7 g plasmolyzed yeast cell was dispersed in 99.8 g limonene oil. And 16.7 g water was directly poured into the suspension with moderate agitation respectively. The formed solid yeast cakes were stored at closed container at 80° C. for 24 h. The starch, as desiccant, was dried to constant moisture content (around 4%) in the oven at 80° C. in advance. The prepared cake was blended with starch in the blender with desiccant/yeast cake mass ratio of 1 and additional SiO2 (e.g. 2%) respectively. The blended mixtures were ground in a ball miller and finally sift the powder to collect the fraction with size above 300 μm. The prepared powders have the size of around average 450 μm, oil loading of around 51% and moisture of 7%. The content of desiccant left in these powders is quantified to be around 10%.

Example 9

66.7 g plasmolyzed yeast cell was dispersed in 120 g peppermint flavor oil. And 80 g water was directly poured into the suspension with moderate agitation respectively. The formed solid yeast cakes were stored at room temperature for 6 days. The AGG maltodextirn 4-8DE, as desiccant, was dried to constant moisture content (around 4%) in the oven at 80° C. in advance. The prepared cake was blended with AGG maltodextrin 4-8DE in the blender with desiccant/yeast cake mass ratio of 2.5 and additional $SiO_2$ (e.g. 2%) respectively. The blended mixtures were sifted to collect the fraction with size above 300 μm. The collected mixture was then ground to the powder with size of around 450 μm, oil loading of around 29%, 8% desiccant, and moisture of 5.3%.

Example 10

66.7 g plasmolyzed yeast cell was dispersed in 120 g berry flavor oil. And 80 g water was directly poured into the suspension with moderate agitation respectively. The formed solid yeast cakes were stored at room temperature for 6 days. The AGG maltodextirn 4-8DE, as desiccant, was dried to constant moisture content (around 4%) in the oven at 80° C. in advance. The prepared cake was blended with AGG maltodextrin 4-8DE in the blender with desiccant/yeast cake mass ratio of 2.5 and additional $SiO_2$ (e.g. 2%) respectively. The blended mixtures were sifted to collect the fraction with size above 300 μm. The collected mixture was then ground to the powder with size of around 450 μm, oil loading of around 30%, 11% desiccant and moisture of 5.5%.

Example 11

66.7 g plasmolyzed yeast cell was dispersed in 120 g lemon pleasant fragrance oil. And 80 g water was directly poured into the suspension with moderate agitation respectively. The formed solid yeast cakes were stored at room temperature for 6 days. The AGG maltodextirn 4-8DE, as desiccant, was dried to constant moisture content (around 4%) in the oven at 80° C. in advance. The prepared cake was blended with AGG maltodextrin 4-8DE in the blender with maltodextirn/yeast cake mass ratio of 2.5 and additional $SiO_2$ (e.g. 2%) respectively. The blended mixtures were sifted to collect the fraction with size above 300 μm. The collected mixture was then ground to the powder with size of around 450 μm, oil loading of around 27%, 7% desiccant and moisture of 6%.

Example 12

66.7 g plasmolyzed yeast cell was dispersed in 99.8 g limonene oil. And 16.7 g water was directly poured into the suspension with moderate agitation respectively. The formed solid yeast cakes were stored at closed container at 80° C. for 28 h. The AGG maltodextrin 4-8DE, as desiccant, was dried to constant moisture content (around 4%) in the oven at 80° C. in advance. The prepared cake was blended with AGG maltodextrin 4-8DE in the blender with maltodextrin/yeast cake mass ratio of 1 and additional SiO2 (e.g. 2%) respectively. The blended mixtures were ground in a ball miller and finally sift the powder to collect the fraction with size above 300 μm. The prepared powders have the size of around average 450 μm, oil loading of around 58%, 10% desiccant and moisture of 5%.

Example 13

99.8 g menthol was heated to 60° C. and 66.7 g plasmolyzed yeast cell was dispersed in it. And 16.7 g water was directly poured into the suspension with moderate agitation respectively. The formed solid yeast cakes were stored at closed container at 80° C. for 16 h. The AGG maltodextrin 4-8DE, as desiccant, was dried to constant moisture content (around 4%) in the oven at 80° C. in advance. The prepared cake was blended with AGG maltodextrin 4-8DE in the blender with desiccant/yeast cake mass ratio of 1 and additional $SiO_2$ (e.g. 2%) respectively. The blended mixtures were ground in a ball miller and finally sift the powder to collect the fraction with size above 300 μm. The prepared powders have the size of around average 450 μm, oil loading of around 45%, 5% desiccant and moisture of 6%.

Example 14

49.5 g menthol and 0.5 g 2-(p-tolyloxy)-N-(1H-pyrazol-5-yl)-N-((thiophen-2-yl)methyl)acetamide was heated to 60° C. and 50 g plasmolyzed yeast cell was dispersed in it. And 12.5 g water was directly poured into the suspension with moderate agitation respectively. The formed solid yeast cakes were stored at closed container at 80° C. for 16 h. The maltodextrin 4-8DE, as desiccant, was dried to constant moisture content (around 4%) in the oven at 80° C. in advance. The prepared cake was blended with maltodextrin 4-8DE in the blender with desiccant/yeast cake mass ratio of 1 and additional $SiO_2$ (e.g. 2%) respectively. The blended mixtures were ground in a ball miller and finally sift the powder to collect the fraction with size above 100 m. The prepared powders have the size of around average 200 m, menthol loading of around 40.65%, freezestrom loading of around 0.45%, 6% desiccant and moisture of 6%.

Example 15

50 g plasmolyzed yeast cell was dispersed in 50 g blackpepper oil. And 12.5 g water was directly poured into the suspension with moderate agitation respectively. The formed solid yeast cakes were stored at closed container at 80° C. for 16 h. The maltodextrin 4-8DE, as desiccant, was dried to constant moisture content (around 4%) in the oven at 80° C. in advance. The prepared cake was blended with maltodextrin 4-8DE in the blender with desiccant/yeast cake mass ratio of 1 and additional $SiO_2$ (e.g. 2%) respectively. The blended mixtures were ground in a ball miller and finally sift the powder to collect the fraction with size above 100 μm. The prepared powders have the size of around average 200 μm, blackpepper oil loading of around 47% and 6% desiccant and moisture of 6%.

Example 16

50 g plasmolyzed yeast cell was dispersed in 50 g garlic oil. And 12.5 g water was directly poured into the suspension with moderate agitation respectively. The formed solid yeast cakes were stored at closed container at 80° C. for 16 h. The maltodextrin 4-8DE, as desiccant, was dried to constant moisture content (around 4%) in the oven at 80° C. in advance. The prepared cake was blended with maltodextrin 4-8DE in the blender with desiccant/yeast cake mass ratio of 1 and additional $SiO_2$ (e.g. 2%) respectively. The blended mixtures were ground in a ball miller and finally sift the powder to collect the fraction with size above 100 μm. The prepared powders have the size of around average 200 μm, garlic oil loading of around 39%, 9% desiccant and moisture of 6%.

Example 17

Chewing gum by coating was prepared by below process. Flavor in the chewing gum are the samples in example 14. The iso-load menthol/2-(p-tolyloxy)-N-(1H-pyrazol-5-yl)-N-((thiophen-2-yl)methyl)acetamide was taken as control sample.

TABLE 7

| Ingredients of unflavored chewing gum pellets (core) | |
| --- | --- |
| Ingredients (gum base) | Wt % |
| Balear - T (Cafosa) | 32.2 |
| Sorbitol P | 60.5 |
| Lycasin (80155) | 5.0 |
| Lecithin (954430) | 2.0 |
| Aspartame (911209) | 0.1 |
| Acesulfam K (900202) | 0.2 |

1) Pre-blend sorbitol P, aspartame and acesulfame K.
2) Pre-heat Sigma-blade mixer at 50-55° C., add pre-warmed gum bases (Baleart-T) and half of the pre-blend from first mix for approximately 2 min.
3) Add the remaining powder blend along with the humectants (lycasin and lecithin) and mix for additional 5 min.
4) Laminate to 5 mm thickness and cut to pieces (2 cm×1 cm, ~1 g/piece).

TABLE 8

| Composition of coating syrup for chewing gum | |
| --- | --- |
| Ingredients (coating syrup) | Wt % |
| Maltisorb P200 | 52.77 |
| Gum instant IRX 49345 (946866) | 1.82 |
| Titanium dioxide (939170) | 0.45 |
| Water | 44.96 |
| Flavoring system in final coating syrup | 0.9-2.8 |

1) Mix water, titanium dioxide, gum instant IRX 49345 and maltisorb P200.
2) Heat to 50° C. and add the flavor under continued agitation and maintain for 10 min
3) Mix the samples using a high-performance dispersing instrument (IKA T18 basic Ultra Turrax®) at 24'000 rpm.
4) Mix 200 g chewing gum with 800 g Teflon balls (diameter 2 cm) in a Brucks Pan Coater.
5) At ~40 rpm add manually 3 mL coating syrup (keep coating syrup cover, under continued agitation at 50° C. during the entire process), mix for 60 sec, add ~5 g Maltisorb P35 to initiate crystallization and then dry with air blower.
6) Repeat point 5 two more times.
7) Start automatic coating cycle with 9 sec syrup addition, 60 sec mixing and 60 sec drying (23-26° C. and 25%-30% humidity).
8) Stop cycles (~80-100) when weight gain of the chewing gum is 33-35% (~1.65 g/chewing gum).
9) Leave the chewing gum for one night.
10) Polish the chewing gum in a pan coater by adding 10 g of Capol 600 and tumbling for 1 h.

Figure 2:
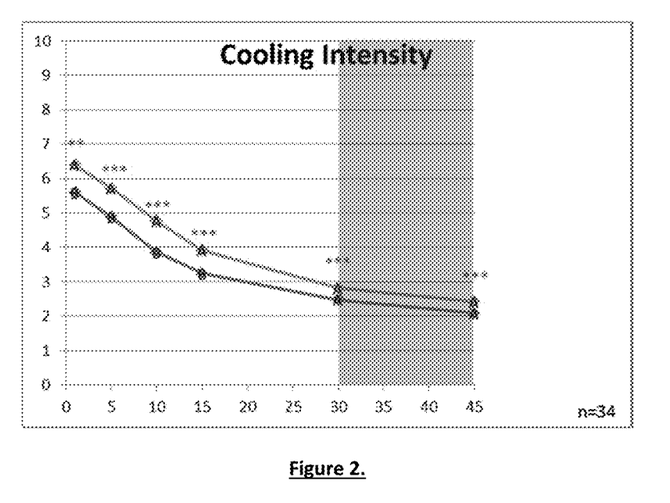
FIG. 2 shows the cooling intensity of chewing gum containing Example 14 (top line) and chewing containing menthol and 2-(p-tolyloxy)-N-(1H-pyrazol-5-yl)-N-((thiophen-2-yl)methyl)acetamide (bottom line).

34 external consumers conducted the sensory test. Chew each sample for a total of 30 minutes with evaluations conducted at 1, 5, 10, 15 and 30 minutes. Remove gum and continue for final evaluation after 45 minutes. Panelists instructed to wait at least two hours between samples. Cooling Intensity ratings on a 10-pt interval intensity scale where 0=Imperceptible and 10=Extremely Pronounced. The scores were analyzed by ANOVA with Post Hoc Duncan's Test (FIG. 2). It clearly showed that cooling intensity of example 14 is stronger that the unencapsulated ones.

What is claimed is:

1. A composition comprising a blended powder comprising:
   a) 25% up to 75% of a plasmolysed micro-organism by weight of the total weight of the composition;
   b) at least greater than 20% up to 60%, by weight flavor or fragrance, of the total weight of the composition,
   c) 1% up to 25% desiccant; and
   d) 4% up to about less than 10% water; wherein the mean particle size distribution by weight of the blended powder is greater than 100 micrometer up to 1 millimeter.

2. The composition as recited in claim 1, wherein the plasmolysed micro-organism is from 25% to 60% by weight, of the total weight of the composition.

3. The composition as recited in claim 1, wherein the plasmolysed micro-organism is a yeast.

4. The composition as recited in claim 1, wherein the mean particle size is from 100 to 600 micrometers.

5. The composition as recited in claim 1, wherein the mean particle size is 200 micrometers.

6. The composition of claim 1, wherein the composition comprises:
   a) 25% up to 75% of a plasmolysed micro-organism by weight of the total weight of the composition;
   b) 50% by weight flavor or fragrance, of the total weight of the composition,
   c) 10% desiccant; and
   d) 8% water; wherein the mean particle size distribution by weight of the composition is greater than 100 micrometer up to 1 millimeter.

7. The composition as recited in claim 2, wherein the plasmolysed micro-organism is from 30% to 40% by weight, of the total weight of the composition.

8. The composition as recited in claim 2, wherein the plasmolysed micro-organism is from 30% to 35% by weight, of the total weight of the composition.

9. The composition as recited in claim 2, wherein the plasmolysed micro-organism is 32% by weight, of the total weight of the composition.

10. The composition as recited in claim 4, wherein the mean particle size is from 300 to 600 micrometers.

11. The composition as recited in claim 4, wherein the mean particle size is 450 micrometers.

12. The composition as recited in claim 4, wherein the mean particle size is from 100 to 600 micrometers.

* * * * *